United States Patent [19]

Persoff et al.

[11] Patent Number: 5,311,766
[45] Date of Patent: May 17, 1994

[54] METHOD AND APPARATUS FOR DETERMINING TWO-PHASE FLOW IN ROCK FRACTURE

[75] Inventors: Peter Persoff, Oakland; Karsten Pruess, Berkeley; Larry Myer, Benicia, all of Calif.

[73] Assignee: The United States of America as represented by the United States Department of Energy, Washington, D.C.

[21] Appl. No.: 909,937

[22] Filed: Jul. 7, 1992

[51] Int. Cl.$^5$ .............................................. G01N 15/08
[52] U.S. Cl. ...................................................... 73/38
[58] Field of Search ..................................... 73/38, 153

[56] References Cited

U.S. PATENT DOCUMENTS

| | | | |
|---|---|---|---|
| 2,345,935 | 4/1944 | Hassler | 73/51 |
| 4,506,542 | 3/1985 | Rose | 73/38 |
| 4,716,758 | 1/1988 | Amantini | 73/38 |
| 4,817,423 | 4/1989 | Christiansen | 73/153 |
| 4,868,751 | 9/1989 | Dogru et al. | 364/422 |
| 4,884,438 | 12/1989 | Jones et al. | 73/153 |
| 4,907,442 | 3/1990 | Jones et al. | 73/38 |

OTHER PUBLICATIONS

J. S. Osaba, et al., "Laboratory Measurements of Relative Permeability," Petroleum Transactions, AIME, vol. 192, 1951, pp. 47–56.

W. Rose, "Some Problems in Applying the Hassler Relative Permeability Method," Journal of Petroleum Chemistry, Jul. 1980, pp. 1161–1163.

W. Rose, "Relative Permeability," Petroleum Engineering Handbook, Society of Petroleum Engineers, Richardson, Tex., 1987, Chapter 28.

P. Persoff, et al., "Two-Phase Flow Visualization and Relative Permeability Measurement in Transparent Replicas of Rough-Walled Rock Fractures," LBL-30161 (Lawrence Berkeley Lab-University of California), Jan. 1991.

Primary Examiner—Hezron E. Williams
Assistant Examiner—Valerie Francies
Attorney, Agent, or Firm—Miguel A. Valdes; Roger S. Gaither; William R. Moser

[57] ABSTRACT

An improved method and apparatus as disclosed for measuring the permeability of multiple phases through a rock fracture. The improvement in the method comprises delivering the respective phases through manifolds to uniformly deliver and collect the respective phases to and from opposite edges of the rock fracture in a distributed manner across the edge of the fracture. The improved apparatus comprises first and second manifolds comprising bores extending within porous blocks parallel to the rock fracture for distributing and collecting the wetting phase to and from surfaces of the porous blocks, which respectively face the opposite edges of the rock fracture. The improved apparatus further comprises other manifolds in the form of plenums located adjacent the respective porous blocks for uniform delivery of the non-wetting phase to parallel grooves disposed on the respective surfaces of the porous blocks facing the opposite edges of the rock fracture and generally perpendicular to the rock fracture.

9 Claims, 6 Drawing Sheets

METHOD AND APPARATUS FOR DETERMINING TWO-PHASE FLOW IN ROCK FRACTURE

The invention described herein arose in the course of, or under, Contract No. DE-AC03-76SF00098 between the United States Department of Energy and the University of California.

BACKGROUND OF THE INVENTION

This invention relates to a method and apparatus for measuring the permeability of a rock fracture to two or more immiscible fluids. More particularly, this invention relates to a method and apparatus for measuring the permeability of a rock fracture to two flowing phases such as a liquid and a gas.

Data on the relative permeability of a rock fracture to two or more immiscible fluids, such as a liquid and a gas, is needed in predicting fluid flow in such processes as nuclear waste isolation, petroleum reservoir engineering, and exploitation of geothermal energy. When two phases occupy a porous medium or a fracture, in general one phase wets the surface better than the other. The non-wetting phase must, therefore, be at a higher pressure; and the difference in pressure is called the capillary pressure.

In measuring two-phase flow, the capillary pressure must be uniform throughout the flow field, or errors result which are difficult to compensate for. A method to achieve uniform capillary pressure, when measuring the permeability of porous bodies, is disclosed in Hassler U.S. Pat. No. 2,345,935, wherein the wetting phase is fed to and from the porous sample body through solid end blocks placed respectively against the opposite ends of the porous sample body. A circular distribution groove, intersecting a bore passing through the end block, is formed in the respective face of each end block facing the porous sample body, and porous material is respectively placed in each of these circular distribution grooves so that the wetting phase must pass through this porous material in the end blocks before reaching the face of the porous sample body. The non-wetting phase (e.g., a gas) is fed directly to the face of the porous sample body through a bore which passes through the end block to the face of the porous sample body.

A somewhat similar system for measuring the relative permeability of fluids in a porous body is described in Rose U.S. Pat. No. 4,506,542, wherein the end blocks, however, are made of porous material, and the distribution grooves of Hassler are eliminated, with the wetting phase passing directly through the porous end blocks to and from the respective faces of the porous sample body.

However, while the distribution grooves containing porous material in the end blocks of Hassler and the porous end blocks of Rose do provide some distribution of the wetting phase into the porous body to be measured, the use of a single port in the end block of either Rose or Hassler to deliver the non-wetting phase to the face of the porous body leaves something to be desired, particular when one attempts to measure the permeability of a fracture in a rock structure, rather than the permeability of a porous body wherein the porous nature of the body being studied may itself provide a certain degree of distribution means for the non-wetting phase.

Osaba et al., in an article entitled "Laboratory Measurements of Relative Permeability", published in Petroleum Transactions, AIME, Volume 192 (1951), at pages 47–56, describe the measurement of the relative permeabilities to oil and gas on small core samples of reservoir rock and illustrate apparatus for making measurements by the Hassler method using semi-permeable discs at each end of the core sample to allow oil, but not gas, to pass. Provision is made for gas to enter and leave the core sample through radial grooves in the respective faces of the semipermeable discs.

In the study of porous materials, the distribution of the wetting and non-wetting phases to the face of the porous sample is not critical, because the three-dimensional network of pores within the sample ensures that essentially all pores have access to either phase, and will be occupied by one phase or the other as determined by capillary pressure. For a fracture, however, there is no such three-dimensional network of pores to accomplish the detailed distribution of the phases, so the uniform delivery of both the wetting and non-wetting phases to all parts of the fracture edge is necessary to obtain accurate results.

Measurement of fluid flow through a rock fracture has been previously measured. Jones et al. U.S. Pat. No. 4,884,438 describes the measurement of flow of a single phase through a fracture using inlet and outlet blocks which respectively contain inlet and outlet ports for transporting the fluid to and from the fracture face.

The determination of fluid saturation within a fracture is taught in Jones et al. U.S. Pat. No. 4,907,442, by establishing a functional relationship between fluid saturation and electrical capacitance for a multiple component fluid and then, after introducing the fluid between the fracture faces of the fractured media, the fluid saturation is determined from electrical capacitance measurements.

However, it would be desirable to provide a reliable method and apparatus for measuring multiple phase flow in a single fracture wherein both wetting and non-wetting phase are delivered to, and uniformly distributed across, opposite edges of a fracture in a manner which will permit accurate determination of the flow rates and pressure drops of the respective phases through the fracture to determine the permeability of the fracture, and measurement of the capillary pressure at the inlet and outlet edges of the fracture.

In a paper entitled "Two-Phase Flow Visualization and Relative Permeability Measurements in Transparent Replicas of Rough-Walled Rock Fractures", published by Lawrence Berkeley Laboratory as LBL-30161, and the contents of which were distributed in a printed publication in January, 1991, we discussed the use of porous end blocks placed against opposite edges of a rock fracture for delivery of a wetting phase to the rock fracture and grooves alternate with flats on the face of the porous block facing the fracture edge to deliver a non-wetting phase to the fracture edge.

SUMMARY OF THE INVENTION

It is, however, an object of the present invention to provide an improved method and apparatus for measuring the relative permeability of a rock fracture to multiple phase in a manner which will provide even more uniform delivery of both wetting and non-wetting phases to the fracture edge.

It is another object of the invention to provide an improved method and apparatus for measuring the permeability of multiple phases through a rock fracture which comprises delivering the respective phases through manifold means to uniformly deliver the respective phases to and from opposite edges of the rock fracture in a distributed manner across the gap of the fracture wherein the manifold means for delivering the wetting phase comprises porous block means having a side facing the rock fracture edge and bore means therein for providing uniform distribution of the wetting phase to the porous block surfaces, and the manifold means for delivering the non-wetting phase include a plenum in communication with parallel grooves disposed on a surface of the porous means facing perpendicular to the rock fracture edge.

These and other objects of the invention will be apparent from the following description and accompanying drawings.

DETAILED DESCRIPTION OF THE INVENTION

Figure 1:
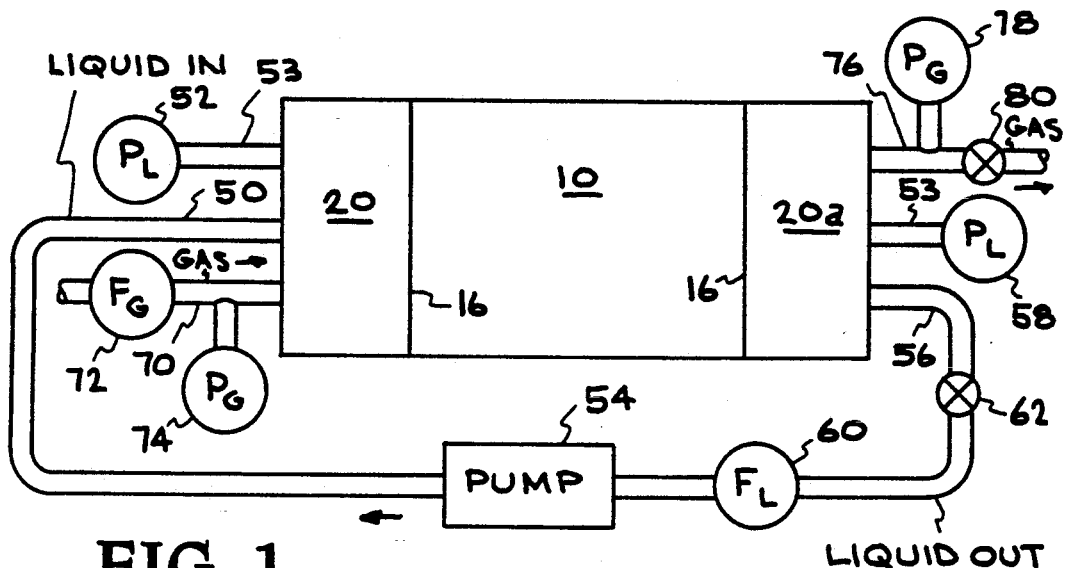
FIG. 1 is a plan view showing in general the apparatus used to control and measure the flow and pressure of a wetting phase and a non-wetting phase through a rock fracture.

Turning now to FIG. 1, the method and apparatus of the invention is schematically illustrated, wherein a sample 10 containing the rock fracture is mounted between two end caps designated in FIG. 1 as 20 and 20a, but which are identically formed and therefore interchangeable. End caps 20 and 20a, which will be described in more detail below, each include a porous distribution member therein into which a wetting phase is delivered for distribution to the edge of the rock fracture in sample 10.

The wetting phase, such as a liquid, is delivered to end block 20 via a conduit 50. One or more pressure monitoring devices 52 monitor and record the pressure of the wetting phase delivered through conduit 50 at the interface between sample 10 and end block 20, i.e., the wetting phase pressure as it enters the fracture in sample 10. The wetting phase passes through the rock fracture in sample 10, enters end block 20a, and then exits end block 20a via conduit 56.

It should be noted at this point that the wetting phase usually (but not always) will be a liquid phase, while the non-wetting phase will usually (but not always) be a gas phase. For example, as an exception to the above, when mercury and air constitute the two phases, air would be the wetting phase, while mercury would be the non-wetting phase. Another exception could be that of wetting and non-wetting liquids, e.g., oil and water. In any event, whether one or both phases constitute a liquid, it may be advisable to add a biocide to the liquid to inhibit the growth of microorganisms in the fracture which could interfere with the permeability measurements.

One or more pressure monitoring devices 58 then monitor and record the pressure of the wetting phase at the interface between sample 10 and end block 20a, i.e., the pressure of the wetting phase as it leaves the fracture. The wetting phase passes through a flow monitoring device 60 which monitors and records the flow of the wetting phase through conduit 56 before the wetting phase reaches pump 54 which recirculates the wetting phase back to end block 20 via conduit 50 to complete the closed wetting phase circulation loop. A needle valve 62 in wetting phase outlet conduit 56 may be used to permit adjustment of the wetting phase pressure.

At the same time as the wetting phase flows through the rock fracture in sample 10, a non-wetting phase, such as a gas, is flowed to the face of the rock fracture in sample 10 through a manifold system in end block 20, as will be described in more detail below. For illustrative purposes only, the manifold system is shown as a dotted line leading to the interface between end block 20 and sample 10 merely to show that the non-wetting phase is supplied directly to the rock fracture face of sample 10. The non-wetting phase is fed to end block 20 through a conduit 70 and flow monitoring device 72 which monitors and records the flow of the non-wetting phase through conduit 70 before the non-wetting phase reaches end block 20 and sample 10. A pressure monitoring member 74 monitors and records the pressure of the non-wetting phase as it is delivered to sample 10. Another conduit 76 is connected to the non-wetting phase manifold in end block 20a to collect the non-wetting phase passing into end block 20a from the rock fracture in sample 10, and a pressure monitoring device 78 monitors and records the downstream non-wetting phase pressure leaving the rock fracture in sample 10. A needle valve 80 may be placed in non-wetting phase outlet conduit 76 to control the pressure of the non-wetting phase. Inlet capillary pressure is always greater than zero when both phases are present in the fracture. In order to adjust the outlet capillary pressure to equal the inlet capillary pressure, and thus maintain a uniform capillary pressure condition throughout the fracture, needle valves 62 and 80 are adjusted as needed.

These measurements, respectively, of the flows of the two phases, together with the entrance and exit pressure of each phase, and the known dimensions of the sample, can be used to calculate the permeability of the rock fracture using slight modifications of well known formulas for porous media. In effect, one does not actually calculate the permeability of the fracture; rather one calculates the permeability k of the sample, treating it as a porous medium of width w, length L, and height h. Then the permeability of the fracture is represented by the product of the two numbers h and k. For example, suppose the rock sample is 0.02 m high, and the permeability of the entire sample is measured to be 1 darcy. If the sample were 0.04 m high, it would still contain only one fracture, and the measured permeability would then be only 0.5 darcy, although the fracture is exactly the same. To accurately describe the fracture, however, the reported permeability should be independent of the height of the sample, just as a measurement of permeability of a porous medium would be independent of its height. To avoid the problem of having measured permeability dependent on sample height, the product hk, which is constant, descriptive of the fracture, and independent of the sample height, is reported.

The permeability $k_g$ of a porous medium to a compressible fluid such as a gas is calculated by:

$$k_g = \frac{2q_o \mu L p_o}{(p_i^2 - p_o^2)} \quad (1)$$

where $q_o$ is the darcy flow velocity at the outlet, p is the pressure, $\mu$ is the viscosity, L is the length from inlet to outlet, subscripts i and o represent inlet and outlet conditions, respectively, and subscript g refers to gas. Both sides of equation (1) can be multiplied by h to give:

$$hk_g = \frac{2hq_o \mu L p_o}{(p_i^2 - p_o^2)} \quad (2)$$

Without knowledge of the fracture aperture, the value of $q_o$ is not known, but the value of $hq_o$ can be calculated from the known gas flow rate, outlet gas pressure, and sample width:

$$hq_o = \frac{Q_o}{w} \quad (3)$$

where $Q_o$ is the volumetric flow rate [$L^3/t$] and w is the length of the fracture edge at inlet and outlet, i.e., the width of the sample. Substituting equation (3) into equation (2) yields:

$$hk_g = \frac{2\left(\frac{Q_o}{w}\right)\mu L p_o}{(p_i^2 - p_o^2)} \quad (4)$$

Similarly for an incompressible fluid, $k_{liq}$ cannot be measured, but $hk_{liq}$ can be:

$$hk_{liq} = \frac{\frac{Q}{w} \mu L}{p_i - p_o} \quad (5)$$

Since compressible fluids Q and q do not vary from inlet to outlet, subscripts i and o are not used. Note that the right side of equations (4) and (5) can be evaluated without knowing the sample height.

Figure 2:
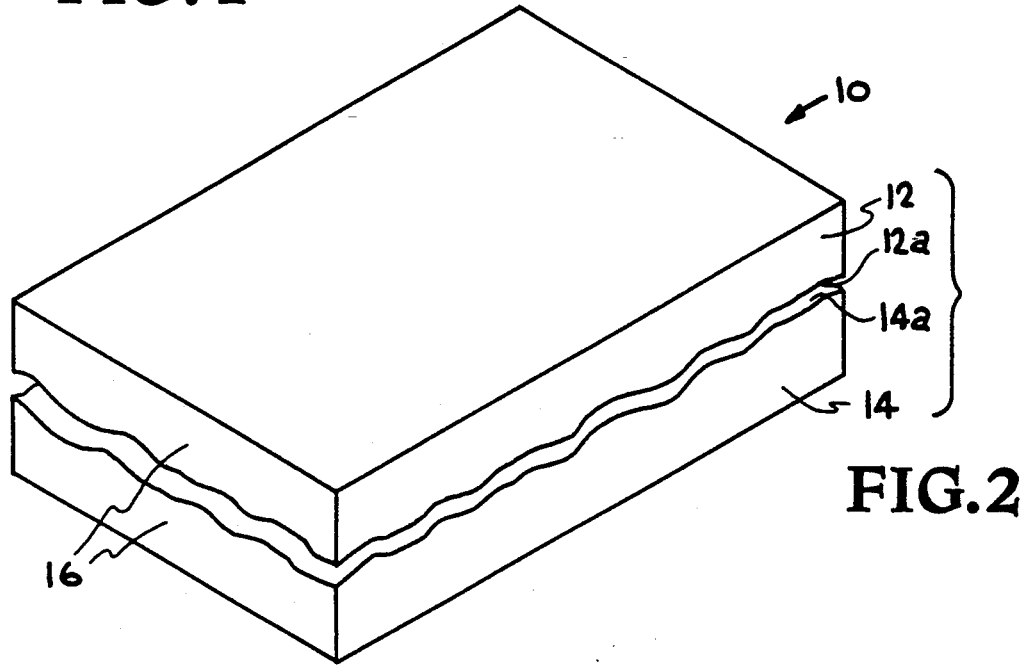
FIG. 2 is an isometric and partially exploded view of two halves of a rock fracture simulated in transparent plastic castings to permit visual and photographic monitoring of the fluid flow through the fracture.
Figure 3:
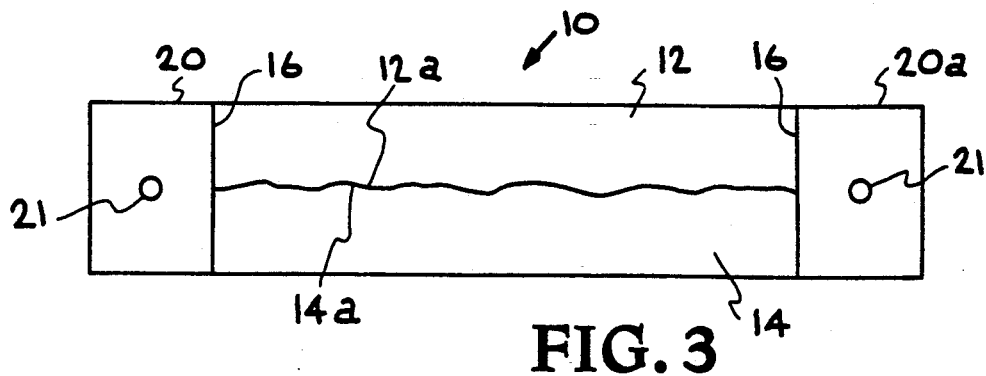
FIG. 3 is a side view of the two halves of the rock fracture of FIG. 2 shown mounted between two end blocks.

FIG. 2 shows sample 10 as comprising an upper portion 12 and a lower portion 14 separated by the fracture comprising upper fracture face 12a and lower fracture face 14a. FIG. 3 is a side view showing rock fracture sample 10 mounted between end blocks 20 and 20a, with an end edge of fracture faces 12a and 14a facing end block 20 and the opposite end edge 16 of fracture faces 12a and 14a facing end block 20a, prior to assembly of the sealing and securement members which will be described below.

In addition to making measurements upon actual rock samples, it is also possible to form a transparent plastic replica of the rock fracture so that the flow of the phases through the fracture may be visually and photographically monitored.

To form such a transparent plastic fracture replica, a mold material, such as a silicone rubber material, may be used to make molds of each side of the fracture, yielding a "negative" of the fracture-wall topography. A silicone rubber material such as, for example, Rhodorsil RTV 1556 silicone rubber available from Rhone-Polenc, Inc. in Monmouth Junction, N.J. may be used to form the "negative" molds. A clear plastic "positive" may then be cast from the molds as a transparent replica of the original rock fracture. As an example, Eccobond 27 clear epoxy, available from Emerson and Cuming, Dewey and Almy Division of W. R. Grace and Company, may be used to form the transparent plastic rock fracture replica samples.

Figure 4:
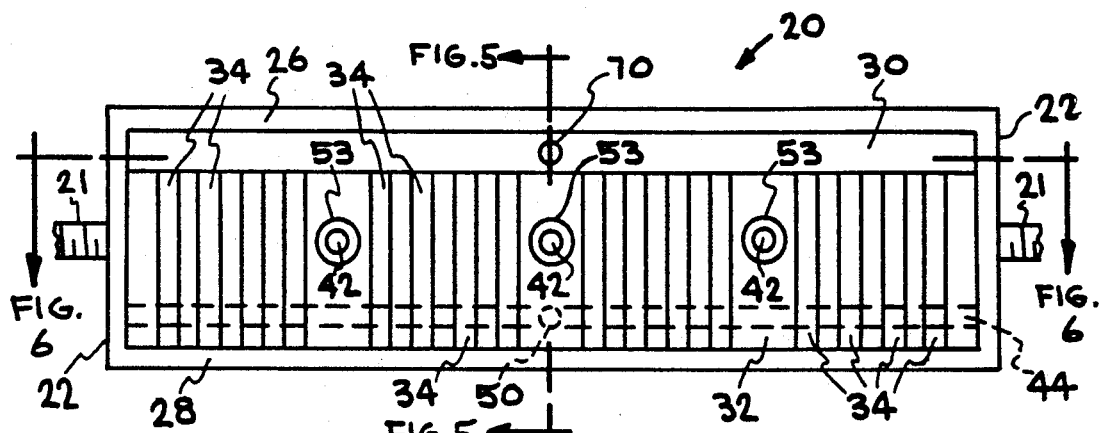
FIG. 4 is a side section view of one of the end blocks showing a porous distribution block mounted in a cavity of the end block for distribution of the wetting phase and showing a manifold used as a part of the uniform distribution of the non-wetting phase fluid across one face of the sample containing the fracture.
Figure 5:
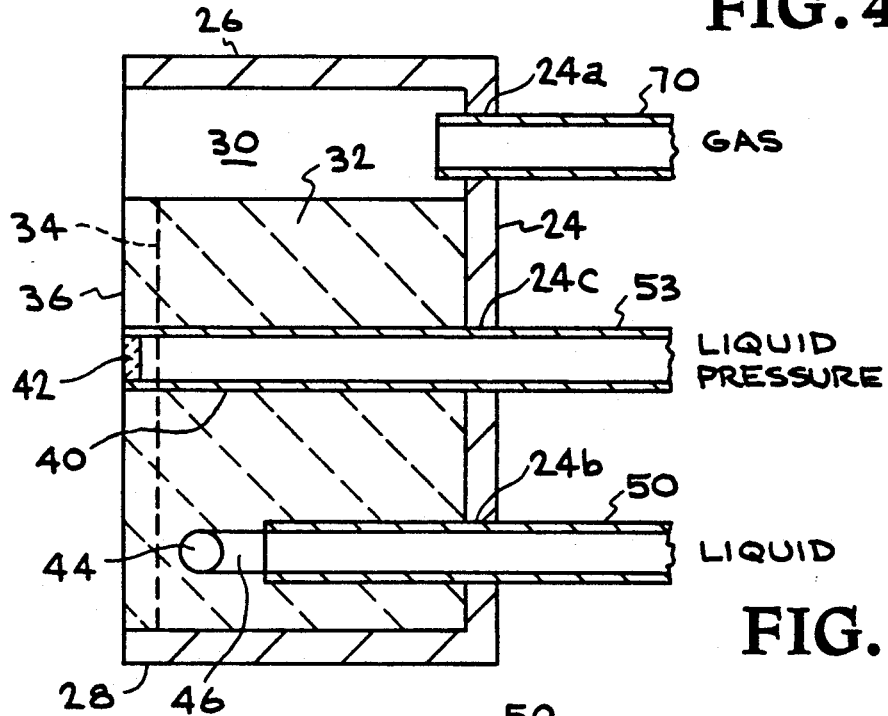
FIG. 5 is a side section view of a portion of the end block of FIG. 4 taken along lines 5—5 and showing the manifold used to distribute the non-wetting phase to the various vertical grooves in the face of the porous body, as well as showing the horizontal cross bore in the porous body used for distributing the wetting phase in the porous body.
Figure 6:
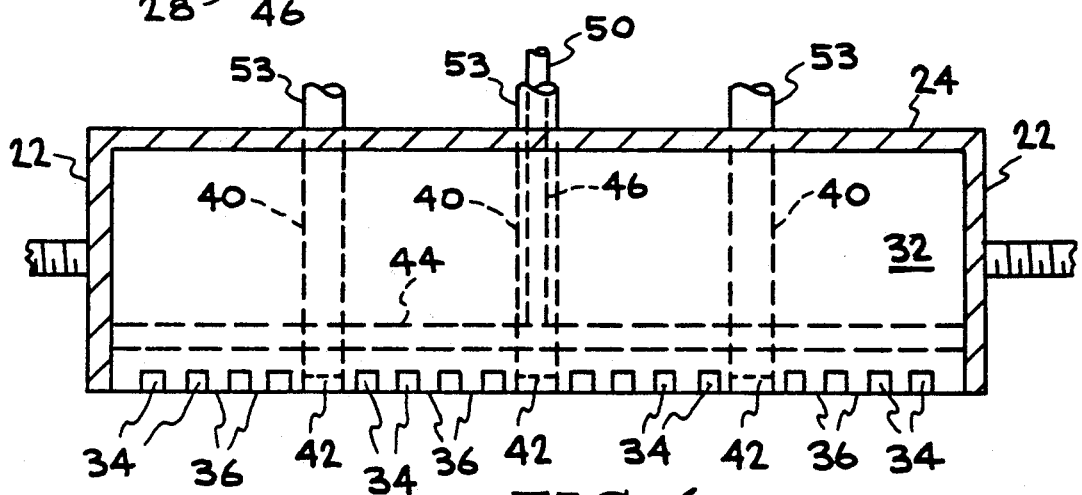
FIG. 6 is a top section view of FIG. 4 taken along lines 6—6 showing the vertical grooves formed in the front face of the porous member facing the fracture edge which are used to distribute the non-wetting phase from the manifold along the fracture gap and showing, in dotted lines, the horizontal cross bore formed in the porous body to distribute the wetting phase in the porous body.

Turning now in particular to FIGS. 4–6, the distribution means within end blocks 20 and 20a for both the non-wetting and wetting phases will be described. Since end blocks 20 and 20a, and the distribution means therein, are essentially duplicates of one another, only end block 20 and the distribution means therein will be described, it being understood that the same structure is present in both end blocks.

End block 20 comprises a rectangular metal member having sidewalls 22, a backwall 24, topwall 26, and bottomwall 28. These walls form a box-like structure with an open front which faces rock fracture sample 10.

Mounted within the box-like structure in end block 20 is a porous block 32 having the same length as the inner dimension of topwall 26 and bottom wall 28, but being somewhat shorter than the inner dimension of sidewalls 22 so as to form a plenum 30 in the box-like structure above porous block 32, as shown in FIGS. 4 and 5. The thickness of porous block 32 is approximately the same as the depth of the box-like structure in end block 20 to backwall 24 so that porous block 32 will fill the opening defined by sidewalls 22, backwall 24, topwall 26, and bottomwall 28, except for the space comprising plenum 30.

The pores of porous block 32 must be essentially of uniform size, and small enough to exclude the entry of the non-wetting phase (e.g. gas) to the porous block even though it enters the fracture at higher pressure than the wetting phase (e.g. liquid) which completely saturates porous block 32. Porous ceramic blocks, with pores of suitable size and uniformity to exclude air at any capillary pressure up to one atmosphere (or higher if desired), are available from Soilmoisture Equipment Corp., Santa Barbara, Calif.

Non-wetting phase conduit 70 passes through a bore 24a in backwall 24 of end block 20 to plenum 30 so that the non-wetting phase from conduit 70 may flow directly into plenum 30. From plenum 30, the incoming non-wetting phase is distributed along the front face of porous block 32 via vertical grooves 34 formed in porous block 32. Grooves 34 are vertically spaced along the front face of porous block 32, and hence across the front face of end block 20 in a manner which will space grooves 34 along end face 16 of rock fracture sample 10 with each groove 34 generally disposed perpendicular to fracture surfaces 12a and 14a in end face 16, as will be appreciated from an examination of FIGS. 3 and 4. In this manner the non-wetting phase may be evenly and uniformly distributed directly across the entire fracture edge in end face 16 of sample 10.

In contrast, the wetting phase transported to end block 20 via conduit 50, is distributed to end face 16 of fracture sample 10 through porous block 32 to achieve the desired uniform distribution of the wetting phase to and along the edge of the fracture in sample 10. Conduit 50 passes through an opening 24b in backwall 24 of end block 20 and then passes through a bore 46 in porous block 32 to a cross bore 44, as shown in FIGS. 4-6, to distribute the wetting phase horizontally along porous block 32 so that the wetting phase can be uniformly delivered to the front surfaces 36 of porous block 32 between grooves 34 for subsequent uniform distribution to end face 16 of fracture sample block 10 and the exposed fracture edge therein.

Cross bore 44 is situated in porous block 32 about 1 mm from the bottom of grooves 34 in porous block 32 so that the wetting phase does not have to traverse the entire thickness or depth of porous block 32 to reach front surface 36 of porous block 32 which is between grooves 34 and which faces end face 16 of sample 10. It will be noted that similar to the transport of the non-wetting phase via grooves 34, the wetting phase is delivered to the fracture edge via parallel front surfaces 36 which are also generally perpendicular to the fracture along the entire length of the fracture edge in end face 16 of sample 10.

The pressure of the wetting phase, at the interface between front surface 36 of porous block 32 and end face 16 of sample 10 is, in the illustrated embodiment, monitored by three pressure gauges through conduits 53 which pass through openings 24c in backwall 24 of end block 20 and fit in bores 40 which pass entirely through porous block 32. Thin porous plugs 42 are fitted into the ends of conduits 53 at front surface 36, to prevent ingress of the non-wetting phase into conduits 53, as seen in FIG. 4-6. Since the response time of the wetting phase pressure measurement is inversely proportional to the thickness of plug 42, the thickness of porous plug 42 is kept to a minimum, e.g., about 1 mm.

Pressure gauge conduits 53 may be bonded in bores 40 in porous block 32 and wetting phase conduit 50 may be bonded in bores 46 in block 32. Block 32, with conduits 50 and 53 attached thereto, may then be assembled to end block 20 by passing conduits 50 and 53 respectively through openings 24b and 24c in backwall 24; and porous block 32 may then be bonded to end block 20 to form a unit.

End block 20, and identically formed end block 20a may now be assembled to end faces 16 of rock fracture sample 10. To secure end blocks 20 and 20a to end faces 16 of sample 10, split metal collars 86 are provided, having openings which accommodate conduits 50, 53, 56, 70, and 76. Screws 88 serve to secure both halves of each split collar together Collars 86 are fastened together respectively behind end blocks 20 and 20a and then are drawn toward one another by tightening nuts 94 on threaded rods 92 which pass through bores 90 in split collars 86 to thereby secure end blocks 20 and 20a to end faces 16 of sample 10.

Before assembling end blocks 20 and 20a to end faces 16 of sample 10, however, it is preferable to provide a compressible porous medium between end face 16 of sample 10 and front surface 36 of porous block 32, respectively mounted in end blocks 20 and 20a, to ensure wetting phase continuity. Filter paper may be used and is placed over the surface 36 of porous block 32 and then wetted. Vertical slits may then be formed with a sharp knife or scalpel in the filter paper corresponding to the location of grooves 34 between the raised front surfaces 36 of porous block 32 so that flow of the non-wetting phase will not be impeded by the presence of the water-saturated porous filter paper.

While pressure and flow measurements of one or both phases could theoretically be made at this point by initiating respective flows of either the non-wetting or wetting phases or both, in practicality, there would be considerable leakage occurring on any or all of the four sides of the interface between end block 20 and sample 10, as well as leakage at the four sides of the interface between sample 10 and end block 20a, and at the side surfaces of sample 10 between top fracture section 12 and bottom fracture section 14. It is, therefore, necessary to provide sealing members at the above intersections to prevent such leakage.

Figure 7:
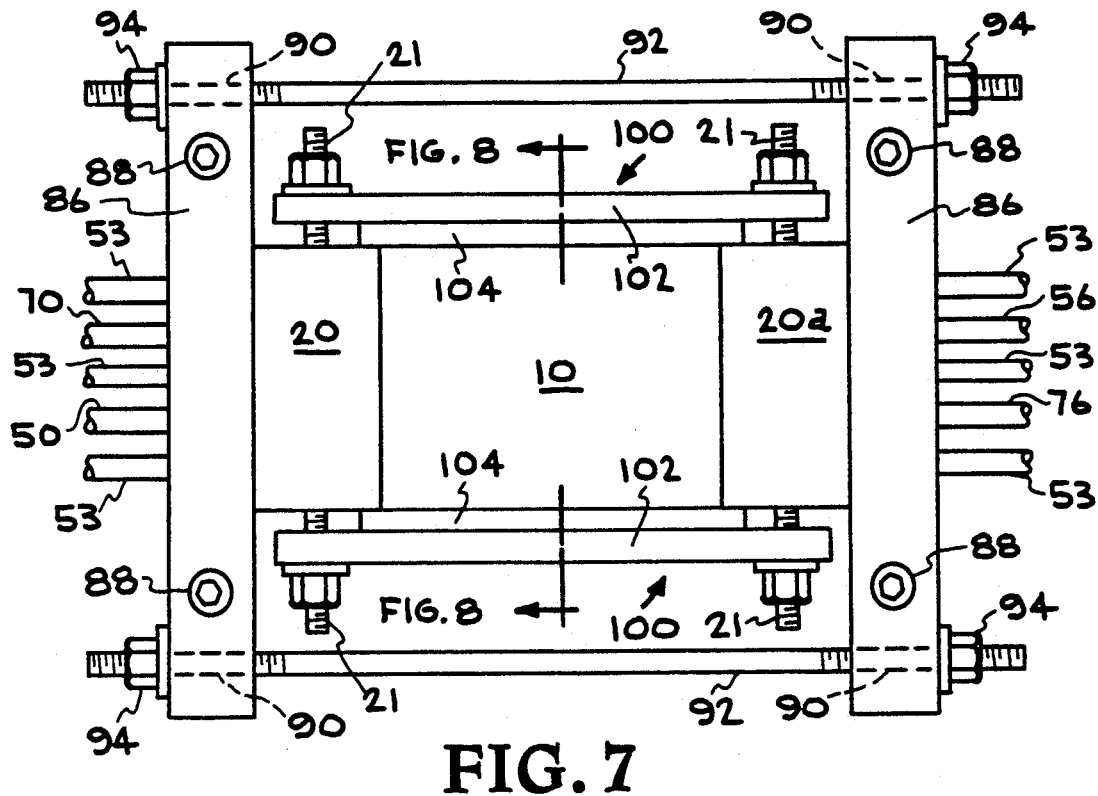
FIG. 7 is a top view showing the fractured rock sample mounted between two end blocks with clamping bars and rods used to draw the two end blocks to the opposite faces of the fracture sample, and sealing bars clamped on the side faces of the fracture sample to seal the side edges of the fracture and the sides of the end surfaces of the fracture sample where such sides of the fracture sample intersect the end blocks.
Figure 8:
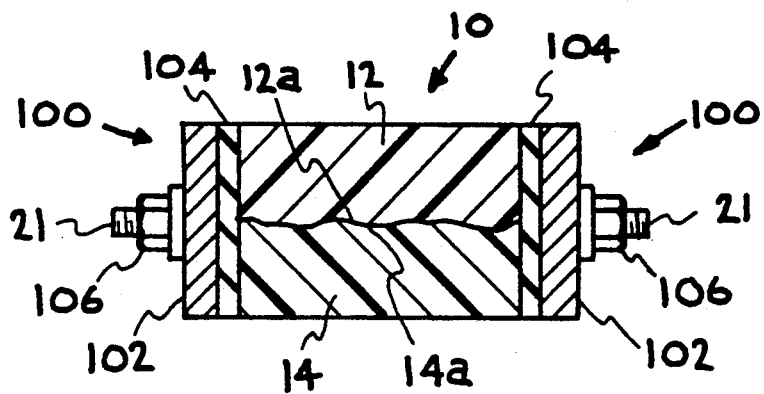
FIG. 8 is an end view of the fractured rock sample of FIG. 7 taken along lines 8—8 to show the mounting of the sealing bars on the side faces of the fracture sample.

Still referring to FIG. 7, the exposed side edge of the fracture on each of the two sides of sample 10, and the exposed edges of the fracture at the intersection between end blocks 20 and 20a with sample 10 may be sealed by sealing members 100 which comprise metal bars 102 having an elastomeric sealing material 104 bonded to one face thereof. Another material which may be used in place of elastomeric sealing material 104 is GelTek strips, available from Raychem in Menlo Park, Calif. Metal bars 102 are provided with holes therein which permit bars 102 to slip over threaded stud shafts 21 on end blocks 20 and 20a. Nuts 106 are then tigthened on threaded shafts 21 to secure sealing members 100 snugly against the side surfaces of sample 10 and end blocks 20 and 20a, as shown in FIGS. 7 and 8, whereby the compression of elastomeric sealing material 104 results in formation of the desired seals. Silicone caulk may be applied to the periphery of face 16 of sample 10 which meets end blocks 20 and 20a. It should also be noted that it is important that elastomeric sealing material 104 overlap the metal surface of end blocks 20 and 20a sufficiently to form the desired seal.

Figure 9:
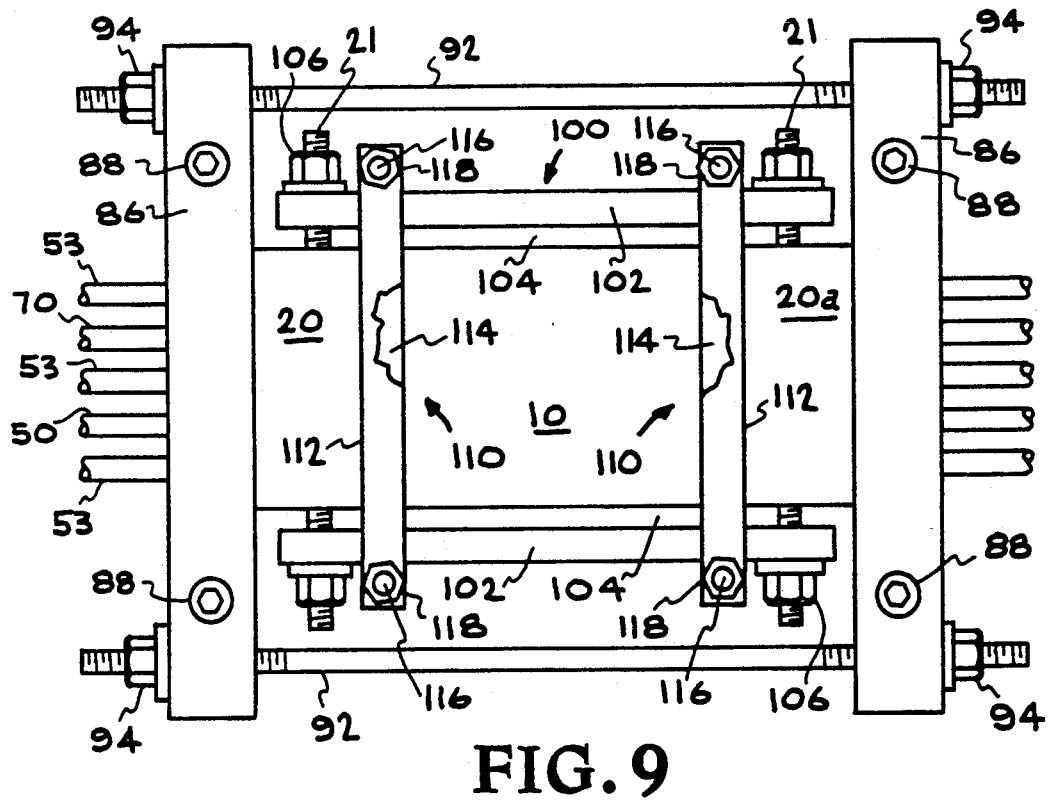
FIG. 9 is a top view similar to FIG. 7, except that sealing bars are also shown which seal the bottom and top edges of the end surfaces of the fractured rock sample where such top and bottom edges intersect the end blocks.
Figure 10:
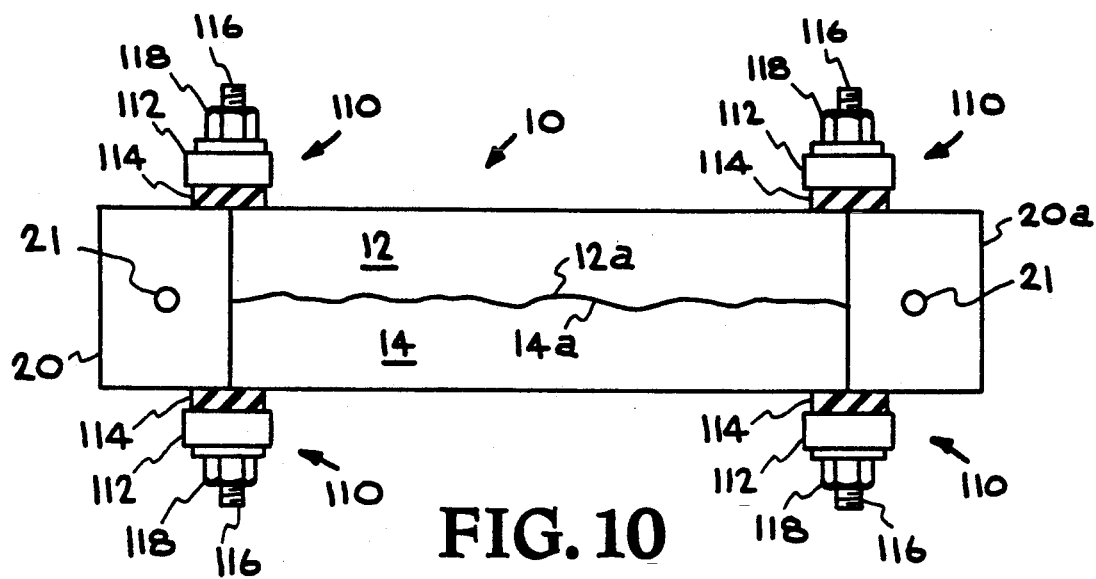
FIG. 10 is a vertical side view showing, in part, the structure of FIG. 9 with sealing bars sealing the top and bottom edges of the fractured rock sample where such edges intersect the end blocks.

Similarly, as shown in FIGS. 9 and 10, four sealing bars 110 are respectively secured to the top an bottom surfaces of end blocks 20 and 20a and sample 10 to seal the interfaces therebetween at the top and bottom edges Sealing members 110 comprise metal bars 112 having elastomeric sealing materials 114 bonded thereto. Threaded shafts 116 pass though openings in metal bars 112 and are provided with nuts 118 to permit tightening whereby the respective top and bottom sealing members 110 are urged toward one another to compress the elastomeric sealing material 114 to seal the top and bottom interfaces between end blocks 20 or 20a and sample 10.

While the use of sealing members 100 and 110 will provide seals for the interfaces between end block 20 and sample 10, end block 20a and sample 10, and between top portion 12 and bottom portion 14 of sample 10, it has been found to be advantageous to provide further securement of top section 12 and bottom section 14 of sample 10 to one another, at least when the fracture is reproduced in transparent plastic, to prevent bulging of central portions of top section 12 and/or bottom section 14 which would otherwise create an artificial widening or enlargement of the width of the fracture between fracture faces 12a and 14a. Such securement also provides known and reproducible compressive loading on the fracture.

Figure 11:
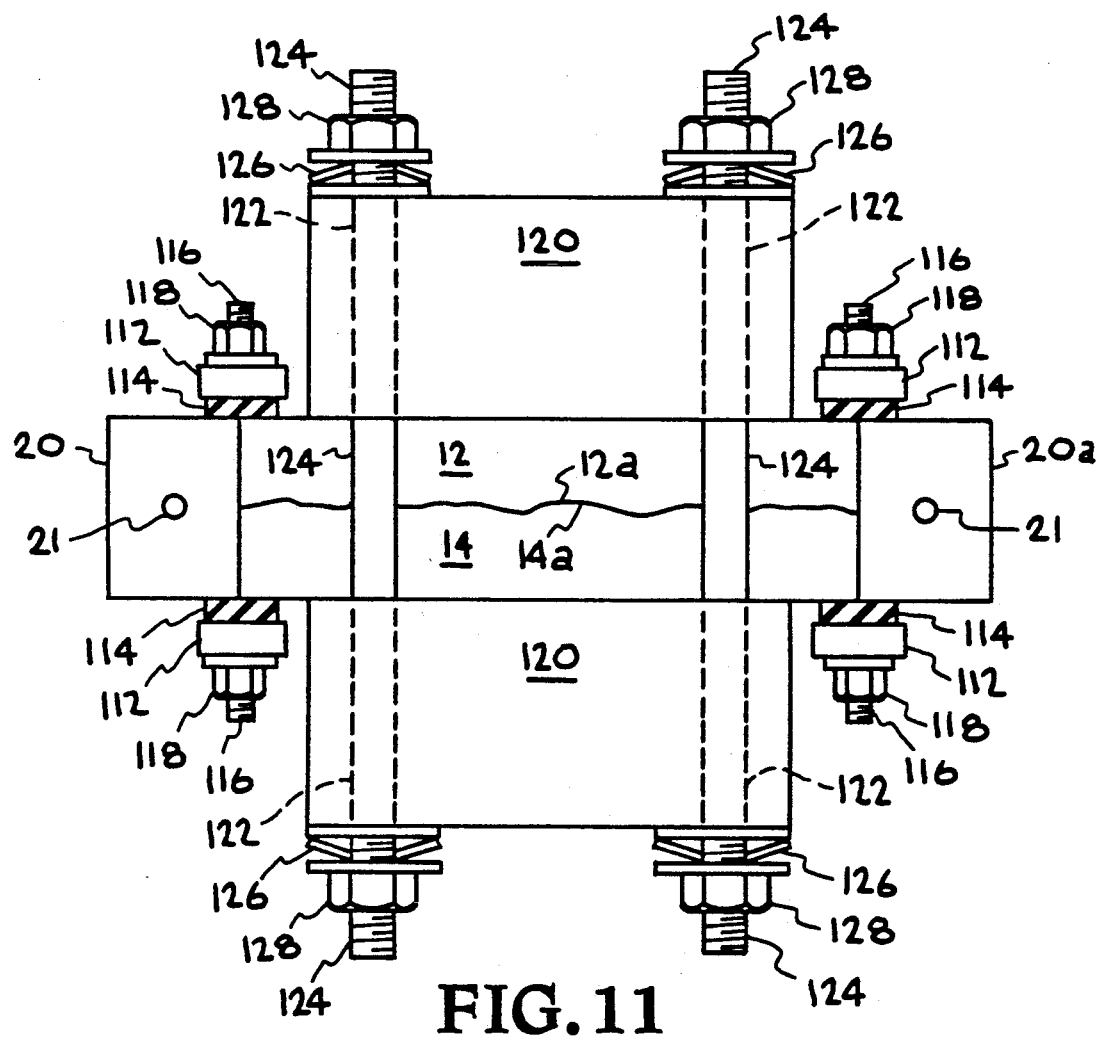
FIG. 11 is a vertical side view similar to that of FIG. 10 except that transparent blocks have been bolted respectively over the outer surfaces of the simulated rock fracture sample halves to prevent any artificial swelling or bulging of the fracture, while preserving visual and photographic monitoring of the fluid flow through the fracture.

As shown in FIG. 11, top section 12 and bottom section 14 may be further secured to one another in compression, without impairing the visual transmission of the flow of the phase or phases through the fracture, by clamping large clear plastic blocks 120, e.g., clear blocks of Lucite plastic, together. Bores 122 in blocks 120 receive threaded shafts 124 and nuts 128 are threaded thereon using Belleville springs 126 to provide a pressure, for example, for a nine square inch rock fracture sample 10, of 240 lb, corresponding to 26.7 psi. The provision of such sealing means, together with sealing members 100 and 110, permit the apparatus to maintain a pressure, without leaks, of 20 psi, when tested with a non-wetting phase, which will be a sufficient pressure to permit collection of the pressure and flow data necessary to calculate the relative permeability of the fracture.

Figure 13:
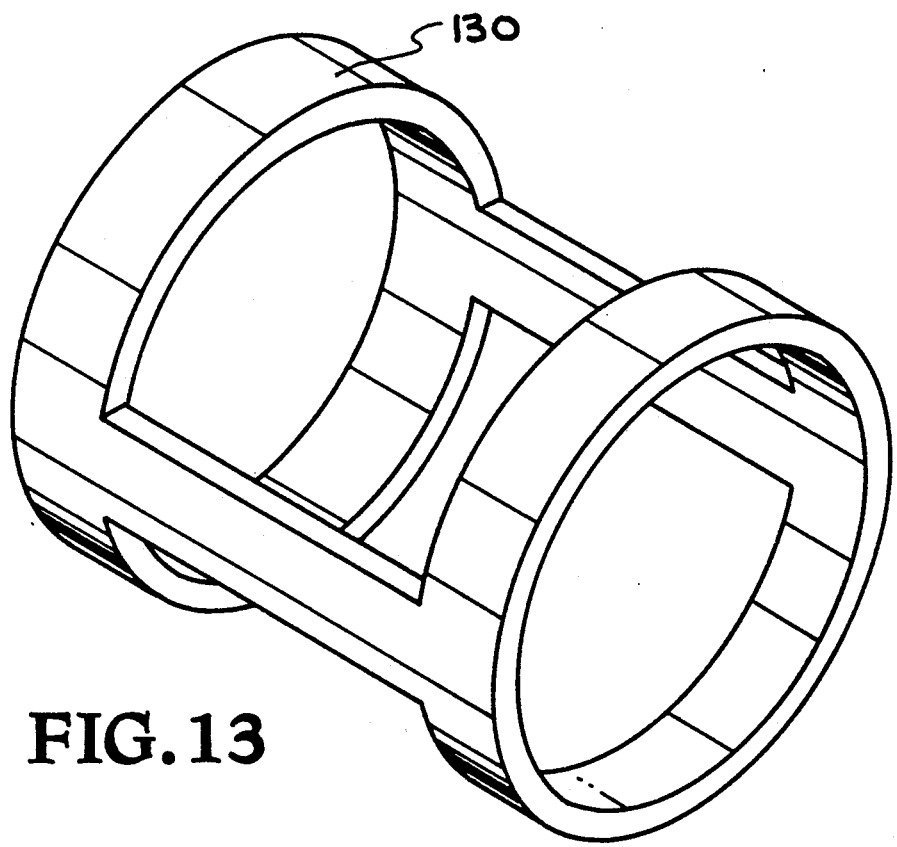
FIG. 13 is an isometric view of the material used to form the unitary elastomeric seal of FIG. 12.
Figure 12:
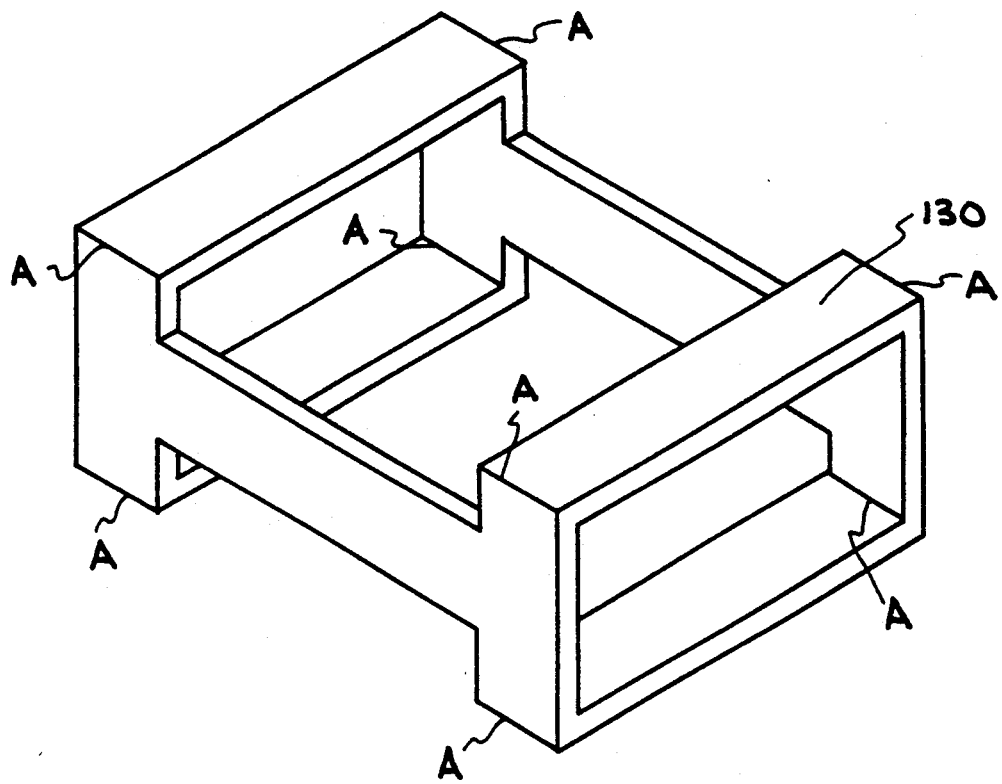
FIG. 12 is an isometric view of a unitary elastomeric sealing material used to seal the edges of the rock fracture sample, showing the potential leakage points in the prior sealing structure.
Figure 14:
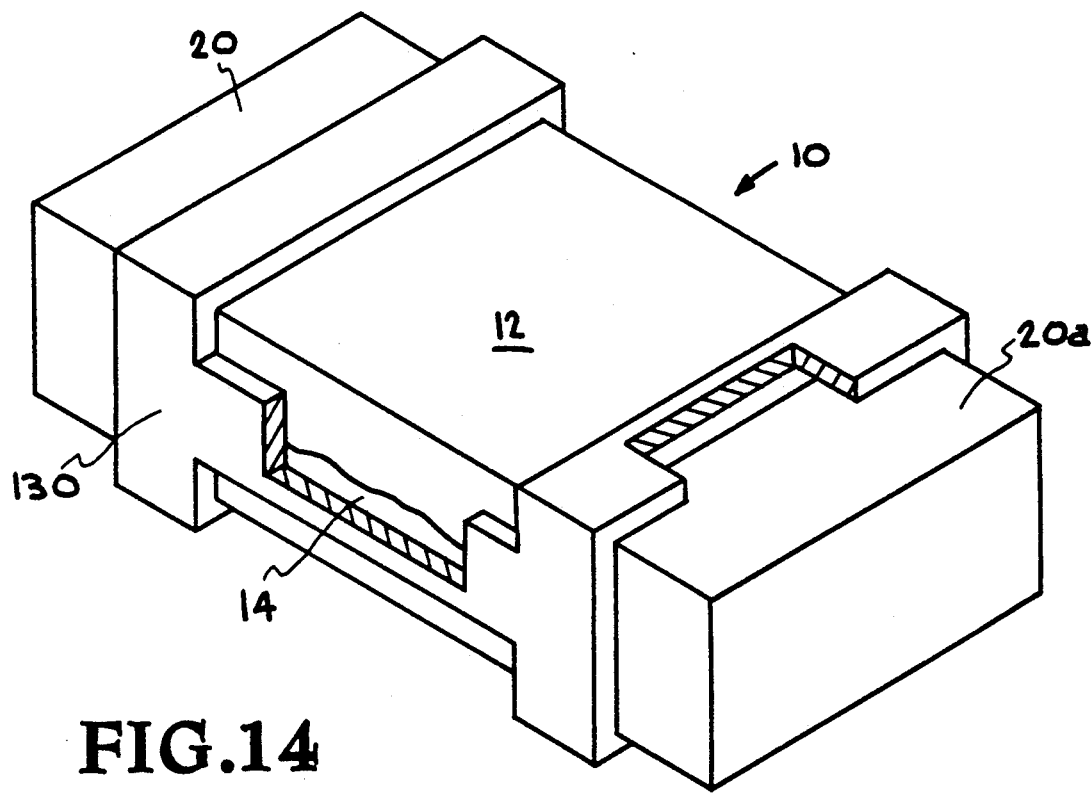
FIG. 14 is an isometric view showing the unitary elastomeric seal of FIG. 12 fitted in place over the edges of the rock fracture sample halves and end blocks; with the fracture sample halves and end blocks depicted as entirely transparent to permit viewing of the fit of the unitary elastomeric seal thereon.

While the just described sealing members 100 and 110 do provide a satisfactory degree of sealing, it has been found that some leakage can occur where the respective seals meet one another, as shown at the eight points designated as A in FIG. 12. This can be effectively eliminated, as shown in FIGS. 12-14, by the substitution of a single or unitary elastomeric sealing structure 130 for sealing materials 104 and 114. This sealing structure 130 is depicted in FIG. 12 as it would look when stretched to fit around sample 10 and end blocks 20 and 20a. The same metal sealing bars 102 and 112 are used, but sealing structure 130 is not bonded to bars 102 and 112. As illustrated in FIG. 13, sealing structure 130 may be initially formed by cutting a tubular section of an elastomeric material. FIG. 14 illustrates the installation of unitary elastomeric sealing structure 130 on the testing apparatus, i.e., around the joints between fractured rock sample 10 and end blocks 20 and 20a, and the joint between upper section 12 and lower section 14 of sample 10, with all structural materials other than sealing structure 130 depicted as transparent to permit a view of the fit of sealing structure 130 at all of the sealing surfaces and interfaces.

To demonstrate the method and apparatus of the invention, "negative" silicone rubber molds were made of a fracture in an 11.5 cm diameter granite sample. The fracture was approximately perpendicular to the axis of the cylindrical sample. 7.6 cm by 7.6 cm clear epoxy resin castings of both sides of the fracture were made from the rubber molds and the castings were then mounted between two end blocks, each having a porous block therein having an average pore size (diameter) of about 2.5 $\mu$m.

Each of the porous blocks had 40 vertical grooves of about 0.040 inch depth cut from top to bottom in the front face of the block. Glass fiber filter paper was placed between the end blocks and the sample with openings cut in the filter paper corresponding to the grooves in the porous blocks. The porous block in the end block terminated about 0.1 inch from the inner surface of the top wall of the end block, leaving a non-wetting phase plenum having a cross section measuring about 0.1 inch by about 3 inches in communication with the vertical grooves to uniformly deliver the non-wetting phase across the face of the end block and hence across the face of the fracture facing the end block. A ⅛" O.D. conduit fed the non-wetting phase to the plenum. The porous block also had a 1/10" diameter horizontal cross bore therein about 1 mm from the bottom surface of the grooves in the front face of the block, with a ⅛" O.D. conduit for the wetting phase communicating with this cross bore to deliver the wetting phase to the porous block.

The apparatus was evacuated to a pressure above the vapor pressure of water, and water was circulated through the wetting phase conduits in the apparatus to saturate the porous blocks and the fracture During this time, the portions of the apparatus designed to be filled with a non-wetting phase were also filled with water (which was later displaced when the non-wetting phase was admitted to the apparatus). The system was pressurized for 24 hours to test for leaks and the recorded pressures during this time indicated that none had occurred. Inlet and outlet wetting phase pressure and flow were recorded for the wetting phase and these measurements, were used, together with the dimensions of the fracture, to calculate the wetting phase permeability of the fracture. The average fracture gap was calculated from the measured permeability.

After measuring the wetting phase permeability of the fracture, two-phase flow was initiated by starting non-wetting phase injection into the fracture. The non-wetting phase displaced the wetting phase in the plenum and in the grooves in the front face of the porous blocks, and made a flow path through the fracture from the non-wetting phase inlet to the non-wetting phase outlet. Visual observations were made and inlet and outlet non-wetting and wetting phase pressures were recorded, as well as the non-wetting phase and wetting phase flow rates. The non-wetting phase flow was then increased and the wetting phase flow rate decreased stepwise to reach a new steady state. For each steady state after the first, the needle valve on the non-wetting phase outlet line was adjusted to get the outlet and inlet capillary pressure approximately equal, and each steady state was maintained for 24 hours or longer before proceeding to the next measurement. Measurements were made at a series of eight flow conditions with non-wetting-to-wetting phase flow rate ratios varying over three orders of magnitude.

The $hk_g$ value for the non-wetting phase permeability through the fracture, and the $hk_{liq}$ for wetting phase permeability through the fracture were calculated using equations (2) and (4) above and relative permeabilities were calculated by normalizing the measured effective non-wetting phase and wetting phase permeabilities to the wetting phase permeability of the fracture.

Table I summarizes the steady-state data measured during single-phase flow and six two-phase flow conditions, measured in order of increasing dryness.

TABLE I

| Flow Rates | | Pressures | | | Capillary Pressures | | Permeabilities | | | |
|---|---|---|---|---|---|---|---|---|---|---|
| $hq_{o,g}$ (m²/s) | $hq_{liq}$ (m²/s) | $P_{g,i}$ (kPa) | $P_{g,o}$ (kPa) | $\Delta P_{liq}$ (kPa) | Inlet (kPa) | Outlet (kPa) | $hk_g$ (m³) | $hk_{liq}$ (m³) | $k_{rel,g}$ | $k_{rel,liq}$ |
| Liquid Flow | | | | | | | | 5.09E-17 | | 1.00 |
| 7.65E-8 | 8.02E-9 | 173.7 | 130.3 | 47.4 | 2.34 | 8.96 | 2.01E-18 | 1.29E-17 | 0.0395 | 0.2530 |
| 1.61E-7 | 8.02E-9 | 179.3 | 126.9 | 52.9 | 2.55 | 2.55 | 3.39E-18 | 1.16E-17 | 0.0666 | 0.2271 |
| 3.15E-7 | 8.02E-9 | 180.6 | 127.6 | 56.7 | 2.97 | 1.86 | 6.58E-18 | 1.08E-17 | 0.1292 | 0.2118 |
| 5.60E-7 | 8.02E-9 | 187.5 | 127.9 | 59.3 | 2.76 | 2.62 | 1.01E-17 | 1.03E-17 | 0.1994 | 0.2026 |
| 1.04E-6 | 8.02E-9 | 199.9 | 128.2 | 70.7 | 3.03 | 1.03 | 1.52E-17 | 8.65E-18 | 0.2970 | 0.1699 |
| 3.30E-6 | 2.73E-9 | 194.8 | 115.5 | 79.4 | 3.03 | 3.24 | 4.13E-17 | 2.62E-18 | 0.8132 | 0.0515 |

Thus the method and apparatus of the invention permit the accurate measurement of the permeability of a rock fracture to two-phase media, such as gas and liquid phases, by providing for the uniform delivery and distribution of both phases across opposite faces of the fracture in a manner which permits accurate determination of the flow rates and pressure drops of the respective phases through the fracture.

While a specific embodiment of the apparatus of the invention for determining two-phase flow in a rock fracture has been illustrated and described for carrying out the method of the invention for determining two-phase flow in a rock fracture, modifications and changes of the apparatus, parameters, materials, etc. will become apparent to those skilled in the art, and it is intended to cover in the appended claims all such modifications and changes which come within the scope of the invention.

What is claimed is:

1. A method for measuring the permeability of one or more phases in a rock fracture sample which includes the steps of:
    a) delivering a first wetting phase uniformly distributed across one edge of said rock fracture through first manifold means within a first porous block, said first manifold means comprising a first bore formed in said first porous block parallel to the surface of said first porous block facing said fracture edge and also parallel to said fracture edge, said first porous block having surfaces on one side thereof facing said rock fracture and in communication with said one edge thereof; said first manifold means, including said first bore, providing uniform distribution of said first wetting phase through said first porous block to said first porous block surfaces for delivery to said one edge of said rock fracture;
    b) uniformly collecting said first wetting phase across an opposite edge of said rock fracture through a second porous block in communication with said opposite edge of said rock fracture and having second manifold means therein to uniformly collect said first phase entering into said second porous block from said opposite edge of said rock fracture, said second manifold means comprising a second bore formed in said second porous block parallel to the surface of said second porous block facing said fracture edge and also parallel to said fracture edge to thereby promote uniform collection of said wetting phase from said fracture edge through said second porous block;
    c) delivering a second non-wetting phase uniformly distributed across said one edge of said rock fracture through a series of parallel grooves formed in said one side of said first porous block facing said one edge of said rock fracture and disposed generally perpendicular to said one edge of said rock fracture to uniformly distribute the delivery of said second non-wetting phase along said one edge of said rock fracture; and
    d) uniformly collecting said second non-wetting phase across said opposite edge of said rock fracture through a second series of parallel grooves formed in said one side of said second porous block facing said opposite edge of said rock fracture, said second parallel grooves disposed generally perpendicular to said opposite edge of said rock fracture to uniformly distribute the collection of said second non-wetting phase along said opposite edge of said rock fracture.

2. The method of claim 1 wherein said step of delivering a second non-wetting phase uniformly distributed across said one edge of said rock fracture further includes delivering said second non-wetting phase to a first plenum means adjacent said first porous block and in communication with all of said parallel grooves in said first porous block.

3. The method of claim 2 wherein said step of uniformly collecting said second non-wetting phase distributed across said opposite edge of said rock fracture further includes collecting said second non-wetting phase from said second series of parallel grooves via a second plenum means disposed adjacent said second porous block and in communication with all of said second parallel grooves in said second porous block.

4. The method of claim 3 which includes the further steps of:

a) measuring the inlet pressure of said first phase at said one edge of said rock fracture;
b) measuring the outlet pressure of said first phase at said opposite edge of said rock fracture;
c) measuring the flow of said first phase through said rock fracture;
d) measuring the inlet pressure of said second phase at said one edge of said rock fracture;
e) measuring the outlet pressure of said second phase at said opposite edge of said rock fracture; and
f) measuring the flow of said second phase through said rock fracture.

5. The method of claim 4 including the further steps of:
a) sealing the interfaces between said rock fracture sample containing said rock fracture edges and said means for delivery and collecting said first and second phases; and
b) sealing side surfaces of said rock fracture sample between said one face and the opposite face of said rock fracture sample.

6. A method for measuring the permeability of one or more phases in a rock fracture with comprises:
a) uniformly delivering a first wetting phase distributed across one edge of a rock fracture through a first manifold comprising a first bore formed within a first porous block facing said one edge of said rock fracture, said first bore disposed parallel to the surface of said first porous block facing said one edge of said fracture and also parallel to said fracture edge to thereby promote uniform distribution of said wetting phase through said first porous block to the entire portion of said one edge of said fracture facing said first porous block;
b) measuring the inlet pressure of said first phase at said one edge of said rock fracture;
c) uniformly collecting said first wetting phase across an opposite edge of said rock fracture through a second porous block and a second manifold comprising a second bore therein facing said opposite edge of said rock fracture, said second bore disposed parallel to the surface of said second porous block facing said opposite edge of said fracture and also parallel to said opposite edge of said fracture to thereby promote uniform collection of said wetting phase by said second porous block from the entire portion of said opposite edge of said fracture facing said second porous block;
d) measuring the outlet pressure of said first phase at said opposite edge of said rock fracture;
e) measuring the flow of said first phase through said rock fracture;
f) uniformly delivering a second non-wetting phase distributed across said one edge of said rock fracture by flowing said second phase through a first plenum to a first series of parallel grooves formed in a side of said first porous block facing said one edge of said rock fracture, said parallel grooves disposed perpendicular to said rock fracture;
g) measuring the inlet pressure of said second phase at said one edge of said rock fracture;
h) uniformly collecting said second non-wetting phase across said opposite edge of said rock fracture by flowing said second phase through a second series of parallel grooves formed in a side of said second porous block facing said opposite edge of said rock fracture and then to a second plenum in communication with said second series of parallel grooves, said second series of parallel grooves also disposed generally perpendicular to said rock fracture;
i) measuring the outlet pressure of said second phase at said opposite edge of said rock fracture; and
j) measuring the flow of said second phase through said rock fracture.

7. Apparatus for measuring the permeability of one or more phases in a rock fracture which comprises:
a) means for delivering a first wetting phase uniformly distributed across one edge of a rock fracture comprising:
   i) a first porous block having surfaces on one side thereof facing said one edge of said rock fracture and in communication with said one edge thereof; and
   ii) first manifold means within said first porous block spaced from said surfaces in communication with said one edge of said rock fracture comprising a first bore disposed parallel to the surface of said first porous block facing said one edge of said fracture and also parallel to said fracture edge to thereby promote uniform distribution of said wetting phase through said first porous block to the entire portion of said one edge of said fracture facing said first porous block;
b) means for uniformly collecting said first wetting phase across an opposite edge of said rock fracture comprising:
   i) a second porous block having surfaces on one side thereof facing an opposite edge of said rock fracture an din communication with said opposite edge thereof; and
   ii) second manifold means within said second porous block spaced from said surfaces in communication with said opposite edge of said rock fracture comprising a second bore disposed parallel to the surface of said second porous block facing said opposite edge of said fracture and also parallel to said opposite fracture edge to thereby promote uniform collection of said wetting phase through said second porous block from the entire portion of said opposite edge of said fracture facing said second porous block;
c) means for delivering a second non-wetting phase uniformly distributed across said one edge of said rock fracture comprising:
   i) a series of parallel grooves formed in said one side of said first porous block facing said one edge of said rock fracture, said parallel grooves disposed generally perpendicular to said rock fracture; and
   ii) first plenum means disposed adjacent said first porous block and in communication with all of said parallel grooves in said first porous block; to evenly distribute the delivery of said second non-wetting phase along said one edge of said rock fracture; and
d) means for uniformly collecting said second non-wetting phase across said opposite edge of said rock fracture comprising:
   i) a second series of parallel grooves formed in said one side of said second porous block facing said opposite edge of said rock fracture, said second parallel grooves disposed generally perpendicular to said opposite edge of said rock fracture; and ii) second plenum means disposed adjacent said second porous block and in communication with all of said parallel grooves in said second porous block;

to evenly distribute the collection of said second non-wetting phase along said opposite edge of said rock fracture.

8. The apparatus of claim 7 which further includes:
a) means for measuring the inlet pressure of said first phase at said one edge of said rock fracture;
b) means for measuring the outlet pressure of said first phase at said opposite edge of said rock fracture;
c) means for measuring the flow of said first phase through said rock fracture;
d) means for measuring the inlet pressure of said second phase at said one edge of said rock fracture;
e) means for measuring the outlet pressure of said second phase at said opposite edge of said rock fracture; and
f) means for measuring the flow of said second phase through said rock fracture.

9. The apparatus of claim 7 which further includes:
a) means for sealing the interfaces between a sample containing said rock fracture and said means for delivery and collecting said first and second phases; and
b) means for sealing side surfaces of said rock fracture sample between said one edge and said opposite edge of said rock fracture.

* * * * *